United States Patent [19]

Hockey et al.

[11] Patent Number: 5,777,469
[45] Date of Patent: Jul. 7, 1998

[54] METHOD AND APPARATUS FOR DETECTING FLAWS IN CONDUCTIVE MATERIAL

[75] Inventors: Ronald L. Hockey; Douglas M. Riechers, both of Richland, Wash.

[73] Assignee: Battelle Memorial Institute, Richland, Wash.

[21] Appl. No.: 691,052

[22] Filed: Aug. 1, 1996

Related U.S. Application Data

[63] Continuation-in-part of Ser. No. 509,551, Jul. 31, 1995, abandoned.

[51] Int. Cl.$^6$ .............................. G01N 27/82; G01R 33/12
[52] U.S. Cl. ........................................... 324/240; 324/238
[58] Field of Search .................................. 324/222, 223, 324/239, 240, 242, 238, 241, 243, 262, 228, 212

[56] References Cited

U.S. PATENT DOCUMENTS

| | | | |
|---|---|---|---|
| 2,519,367 | 8/1950 | Gunn et al. | 324/240 |
| 2,970,256 | 1/1961 | Sazynski et al. | 324/240 |
| 3,881,151 | 4/1975 | Bigelow | 324/226 |

*Primary Examiner*—Walter E. Snow
*Attorney, Agent, or Firm*—Paul W. Zimmerman

[57] ABSTRACT

The present invention uses a magnet in relative motion to a conductive material, and a coil that is stationary with respect to the magnet to measure perturbation or variation in the magnetic field in the presence of an inclusion. The magnet and coil sensor may be on the same side of the conductive material.

16 Claims, 10 Drawing Sheets

DIAGRAM OF HOLES AND NOTCHES IN THICK STEEL DISK

| FLAW NUMBER | THROUGH-WALL HOLE | PERCENT THROUGH-WALL 0.02 INCH DIA. HOLE | 0.02" WIDE NOTCH |
|---|---|---|---|
| 1 | 0.06 INCH DIAMETER | | |
| 2 | 0.052 INCH DIAMETER | | |
| 3 | 0.04 INCH DIAMETER | | |
| 4 | 0.031 INCH DIAMETER | | |
| 5 | 0.02 INCH DIAMETER | | |
| 6 | | 50 (SAME SIDE) | |
| 7 | | 25 (SAME SIDE) | |
| 8 | | 50 (OPPOSITE SIDE) | |
| 9 | | 25 (OPPOSITE SIDE) | |
| 10 | | | 0.01 DEEP |
| 11 | 0.02 INCH DIAMTER | | |

SLOTS ARE 0.031" INCH LONG BY 0.050 INCH WIDE

1. @ 123° SLOT 0.020" DEEP
2. @ 142° SLOT 0.040" DEEP
3. @ 161° SLOT 0.080" DEEP
4. @ 180° SLOT THRU DISK
5. @ 218° HOLE 0.020" DIAMETER
6. @ 231° HOLE 0.031" DIAMETER
7. @ 244° HOLE 0.040" DIAMETER
8. @ 257° HOLE 0.052" DIAMETER
9. @ 270° HOLE 0.060" DIAMETER

10 INCH DIAMETER ALUMINUM DISK, 0.125 INCH THICK

METHOD AND APPARATUS FOR DETECTING FLAWS IN CONDUCTIVE MATERIAL

CROSS REFERENCE TO RELATED INVENTIONS

This application is a continuation-in-part of application Ser. No. 08/509,551 filed Jul. 31, 1995, now abandoned.

This invention was made with Government support under Contract DE-AC06-76RLO 1830 awarded by the U.S. Department of Energy. The Government has certain rights in the invention.

FIELD OF THE INVENTION

The present invention relates generally to a method and apparatus for detecting and/or measuring flaws in conductive material. More specifically, the present invention uses a magnet in relative motion to a conductive material, and a coil that is stationary with respect to the magnet to measure perturbation or variation in the magnetic field in the presence of an inclusion. As used herein, the term "conductive" means electrically conductive. Also, as used herein, the term "flaw" means defect, inclusion, especially non-metallic inclusion, crack or other electrical discontinuity.

BACKGROUND OF THE INVENTION

High volume, high speed production of metal products, for example sheet metal and pipe places demanding requirements on inspection techniques to identify flaws and characterize quality of the metal products. Presently, Faraday eddy current and ultrasonic equipment is used to identify flaws. The eddy current technique is limited to lower production speeds. At production speeds in excess of about 40 ft/sec, bandwidth limitations prevent accurate flaw detection with eddy current techniques. Ultrasonic equipment is limited because it cannot measure electrical resistivity.

U.S. Pat. No. 3,881,151 uses an invariant magnetic field gradient and sensor for detection of flaws in moving electrically conductive objects such as tube, bar, wire, and wire rods. Detectable flaws include laps, cuts, seams and entrapped foreign materials. However, the '151 patent requires a magnetic field gradient and requires that the conductive material to be inspected be passed through a hollow cylindrical magnet. It further requires two sensors for flaw detection.

Figure 1:
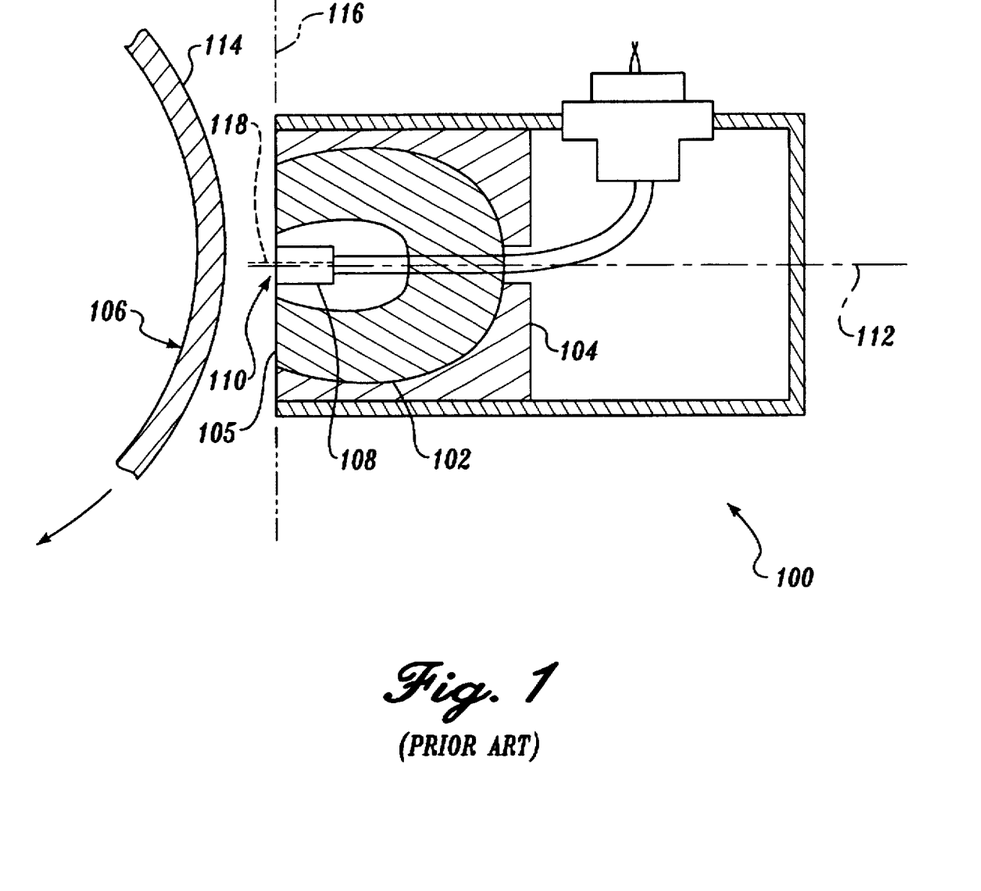
FIG. 1 shows a prior art sensing unit.

U.S. Pat. No. 2,519,367 to Gunn et al. is for a method and apparatus for detecting defects in objects as depicted in FIG. 1 (prior art). The apparatus or sensing unit 100 has a horseshoe magnet 102 embedded in insulating material 104 with the feet 105 of the horseshoe magnet exposed and placed adjacent to one side of the conductive material 106 to be inspected. A single sensing coil 108 is positioned between the legs of the horseshoe magnet 102 and is stationary with respect to the horseshoe magnet 102 by embedment within the insulating material 104 and is also placed adjacent the conductive material 106. Both the magnet 102 and sensing coil 108 are in relative motion with respect to the conductive material 106. An oscilloscope (not shown) receives a signal from the sensing coil 108 when a flaw (not shown) in the conductive material 106 passes by the apparatus 100.

The magnet 102 has a datum point 110 that is a point located on a center line 112 through a center of the magnet and substantially perpendicular to a material surface 114 and on a plane 116 defined by magnet surface(s) (feet 105) facing the material surface 114. The sensing coil 108 has a datum orientation with a longitudinal axis 118 of the sensing coil 108 substantially perpendicular to the material surface 114. In the prior art embodiment of FIG. 1, center line 112 and longitudinal axis 118 are co-linear. They are shown side by side in FIG. 1 for clarity.

Disadvantages of the prior art include (1) limited flaw size detection of flaws having a volume below about 1 mm$^3$, (2) inability to detect subsurface flaws, and (3) inability to quantify flaw area or volume.

SUMMARY OF THE INVENTION

The present invention is an improved sensing unit wherein the sensing coil is positioned away from a datum of either the datum point, the datum orientation, or a combination thereof. Position of the sensing coil away from a datum increases sensitivity for detecting flaws having a characteristic volume less than about 1 mm$^3$, and further permits detection of subsurface flaws. Use of multiple sensing coils permits quantification of flaw area or volume.

It is an object of the present invention to provide an apparatus for quantifying flaw size in conductive material.

It is a yet further object of the present invention to provide an apparatus for detecting subsurface flaws in conductive material or conductive material layers.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 5b is a detail of the sensing unit in FIG. 5a.

DESCRIPTION OF THE PREFERRED EMBODIMENT(S) APPARATUS

Figure 2A:
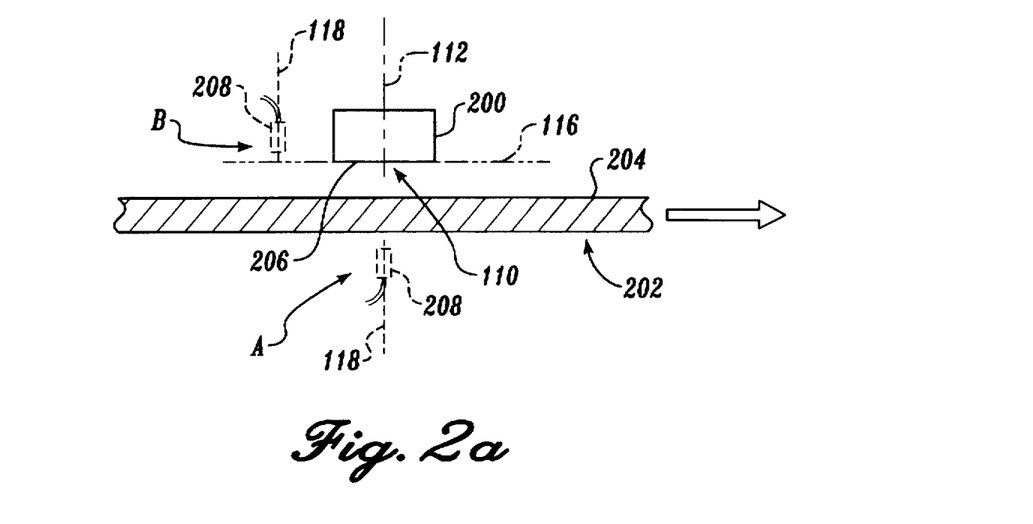
FIG. 2a shows two antidatum embodiments of a sensing unit in accordance with the present invention.

The apparatus of the present invention is a sensing unit for detecting flaws in conductive material. In FIG. 2a, the sensing unit has a magnet 200 having a substantially constant magnetic field, that is placed adjacent to one side of the conductive material 202. The magnet 200 has a datum point 110 defined by an intersection of (1) a center line 112 through a center of the magnet 200 and perpendicular to the material surface 204 with (2) a plane 116 defined by a magnet surface(s) 206 facing the material surface 204. The apparatus further has a sensing coil 208 that is stationary with respect to the magnet 200 wherein the magnet 200 and sensing coil 208 are in relative motion with respect to the conductive material 202. The sensing coil 208 has a longitudinal axis 118 defining a datum orientation of the sensing coil 208.

The present invention is an improvement wherein the sensing coil 208 is positioned away from a datum selected from the group consisting of the datum point 110, the datum orientation and a combination thereof. Specifically, in FIG. 2a, the sensing coil 208 is shown in antidatum locations away from the datum point 110. The first alternative location A is antilateral or on the side of the conductive material 202 opposite the surface 204. The second alternative location B is unilateral or on the same side of the conductive material 202 as the magnet 200, but laterally displaced from the center line 112. In these alternative locations, the sensing coil 208 is exposed to a weaker portion of the magnetic field from the magnet 200 and is therefore able to detect small changes in the magnetic field from smaller flaws. Because it was found that the signal strength was about the same for both alternative locations A and B, it is preferred to place the sensing coil 208 unilaterally with the magnet 200 with respect to the conductive material 202 in alternative location B. In a unilateral position, it is further preferred that the relative motion between the conductive material 202 and the sensing unit be in a direction wherein the magnet 200 "sees" new conductive material 202 ahead of the sensing coil 208 so that the sensing coil 208 "sees" a strong induced current signal.

Figure 2B:
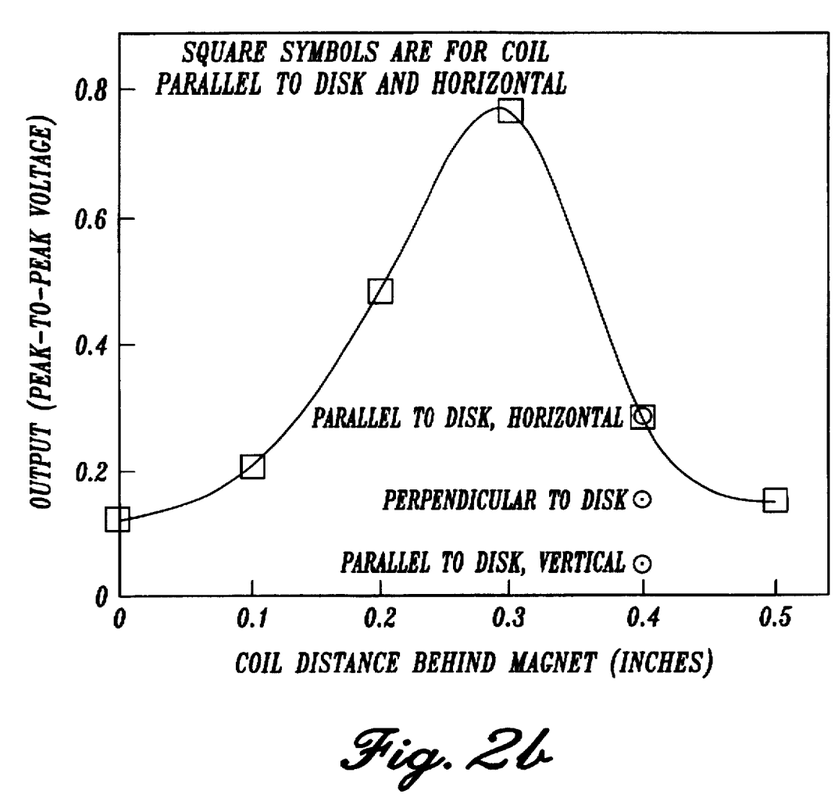
FIG. 2b is a graph of sensing coil output versus spacing between the magnet and the sensing coil.

The spacing or distance between the magnet 200 and sensing coil 208 depends upon the field strength and physical size of the magnet 200, and the sensitivity and size of the sensing coil 208. Nevertheless, for a given sensing unit, there is a spacing that gives a maximum signal from the sensing coil 208. FIG. 2b is a graph of the relationship between signal strength and spacing. The spacing corresponding to the peak 220 is the optimum spacing.

Figure 5:
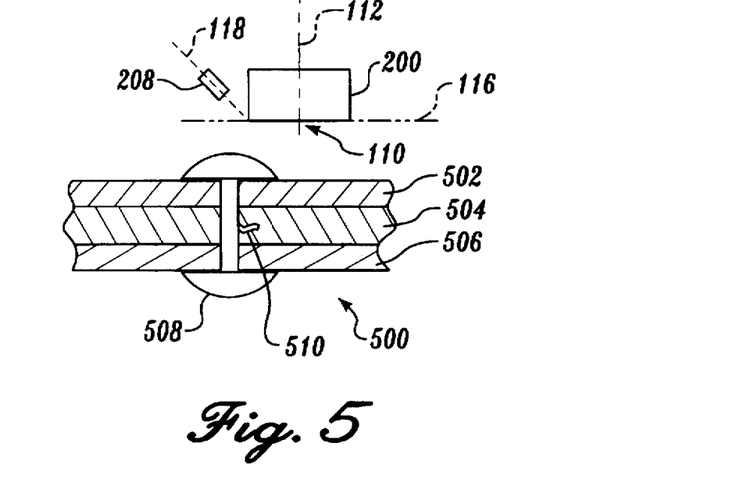
FIG. 5 shows an internal flaw in an assembly of three layers of conductive material held by a rivet.

Having the magnet 200 and the sensing coil 208 unilateral permits detection of flaws in structures that are not accessible on both sides. In particular, aircraft wings are laminate structures held together with rivets. The advent of the present invention makes it possible to inspect the riveted connections of the wings. Aircraft wing inspection is illustrated in FIG. 5. A muli-layered metallic structure 500, for example a wing section, has three layers 502, 504, 506 held together by a rivet 508. A magnet 200 in combination with a sensing coil 208 in a unilateral antidatum relationship are used to detect the flaw 510. Flaw 510 is a subsurface flaw that is generally not detectable by a sensing unit. However, the increased sensitivity of the present invention non-datum positioning or orientation permits detection of subsurface flaws.

Figure 3A:
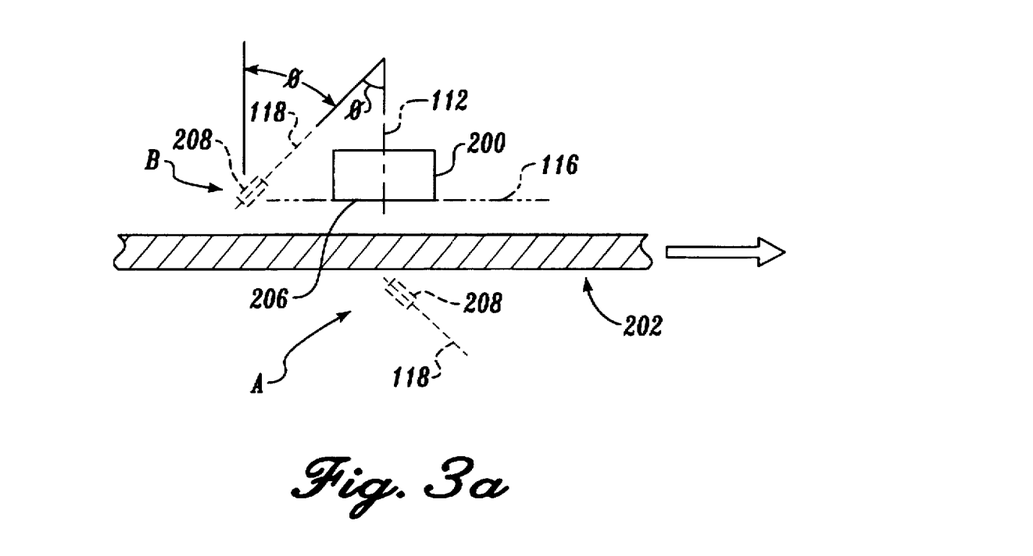
FIG. 3a shows two antidatum and tilted sensor embodiments of a sensing unit in accordance with the present invention.
Figure 3B:
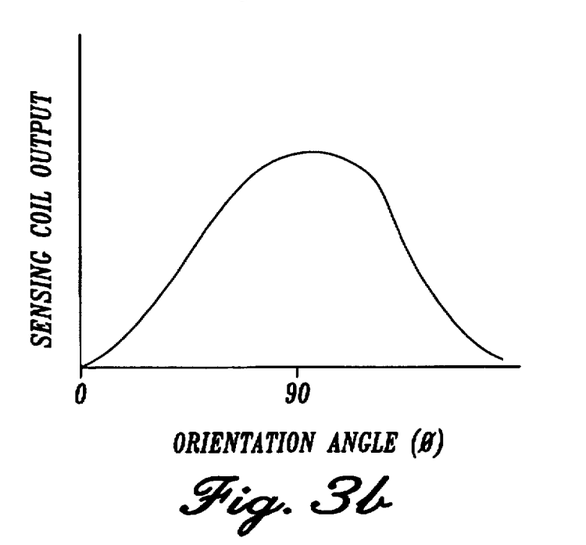
FIG. 3b is a graph of sensing coil output versus orientation angle of the sensing coil.

According to another aspect of the present invention, additional flaw detection sensitivity is achieved by tilting the sensor 208 away from the datum orientation. In FIG. 2a, in both alternative locations A and B, the sensor 208 is in the datum orientation with its longitudinal axis 118 parallel to the center line 112. FIG. 3a shows the sensor 208 tilted from the datum orientation with the longitudinal axis 118 antiparallel with respect to the center line 112. FIG. 3b shows a graph of signal strength as a function of orientation angle phi. The maximum signal strength is achieved with the sensing coil 208 substantially parallel to the conductive material 202 and substantially perpendicular to the center line 112.

Figure 4:
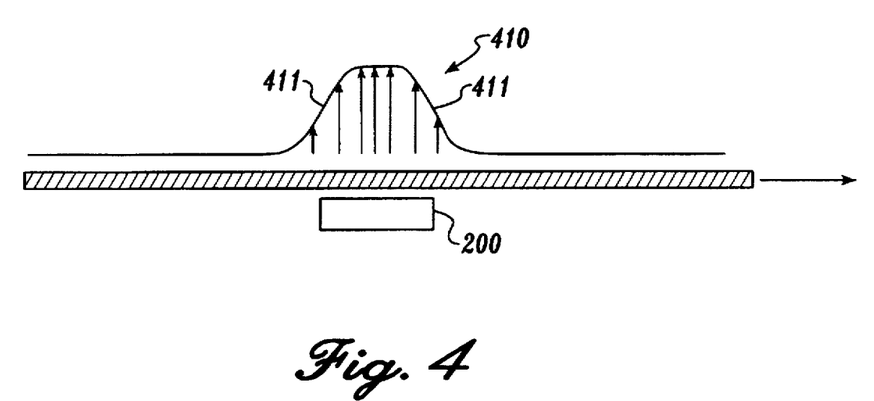
FIG. 4 shows a magnetic field.

The magnet 200 may be any type of electromagnet or permanent magnet. It is preferred that the magnet 200 be a neodymium 27 permanent magnet because of it's high magnetic flux density. The magnet 200 may be of any cross section and any size. It is preferred that the magnet 200 have a substantially square cross section and have a size of less than about 1 inch on a side, preferably less than about ½ inch on a side. FIG. 4 illustrates a substantially constant magnetic field 410. Edge gradients 411 are a result of edge effects, but are not relied upon for measurements nor do they hinder measurements of flaws.

The sensing coil 208 is simply a coil of a conducting material. It is preferred to use copper wire for the coil of conducting material. It is further preferred that the sensing coil 208 be of a size compatible with the size of flaw to be detected. For example detection of a flaw having a dimension of 0.020 inch is preferably done with a sensing coil of about 0.020 inches in length. The coil signal may be increased by inclusion of a conductive core, preferably ferrite. A coil of 0.020 inches may be made with five windings of 0.001 inch diameter copper wire. For purposes of signal strength, the sensing coil should be larger, but for purposes of detecting small inclusions, the sensing coil should be smaller. Hence, one skilled in the art of flaw detection will select a sensing coil size by trading off the benefits of signal strength and inclusion size limit. It is possible to detect very small (0.001 inch) inclusions with a 0.020 inch sensing coil. However, the signal to noise ratio diminishes with flaw size making it more difficult to separate the signal from the noise. However, noise can be reduced by making multiple passes of the flaw past the sensing unit. Because the noise is random, and the flaw signal is repetitive, multiple passes may be used to discern the flaw signal. This repetitive technique is referred to as "stacking". Moreover, optimal orientation of the sensing coil 208 increases the flaw signal strength.

Signals from the sensing coil may be small. Accordingly, a buffer and amplifier may be used to increase the signal strength prior to entering the data acquisition system.

Figure 5A:
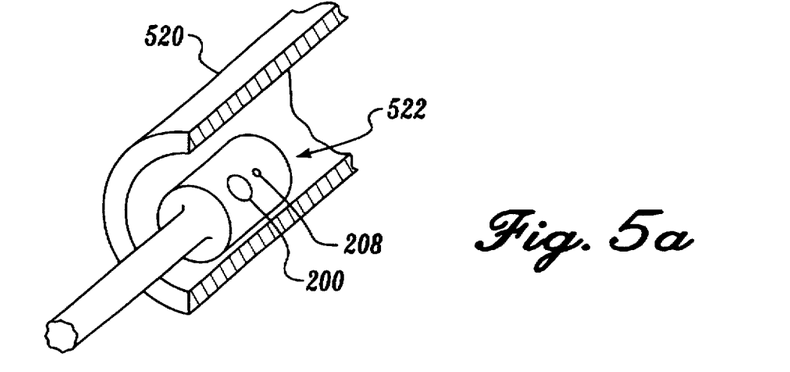
FIG. 5a shows a sensing unit useful for inspecting hollow cylinders.
Figure 5B:
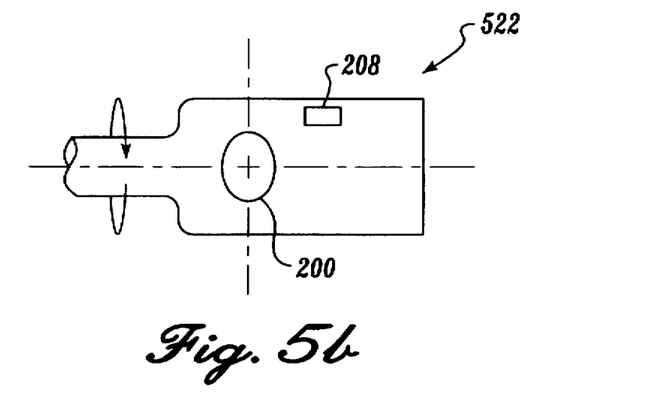

A further embodiment of the present invention is shown in FIG. 5a for inspecting a tube 520. A spindle 522 containing a magnet 200 and a sensing coil 208 in a unilateral antidatum relationship constitutes a sensing unit. The sensing unit is rotated and may also be advanced longitudinally through the tube 520. It is preferred that the sensing coil 208 be "behind" the magnet 200 with respect to the direction of rotation of the spindle 522 as shown in FIG. 5b. It is further preferred that the sensing coil 208 be oriented parallel to the pipe surface as depicted in FIG. 5b.

METHOD

The method of the present invention has the steps of placing a magnet 200 having a substantially constant magnetic field adjacent to one side of a conductive material 202, placing a single sensing coil 208 that is stationary with respect to the magnet 200 wherein the magnet 200 and sensing coil 208 are in relative motion with respect to the conductive material 202, and connecting the sensing coil 208 to a data acquisition system for receiving a signal from the sensing coil 208 when a flaw in the conductive material passes by the magnet 200.

In operation, a magnet 200 and sensing coil 208 are stationary while the conductive material 202 passes by. Alternatively, the magnet 200 and sensing coil 208 are moved past a stationary conductive material 202. When a flaw or inclusion passes by the magnet 200, the magnetic field is perturbed thereby inducing a signal in the sensing coil 208. The signal is measured as a voltage by a data acquisition system.

EXAMPLE 1

An experiment was conducted to demonstrate operation of the present invention. A one inch square neodymium 27 magnet with a 0.020 inch sensing coil were used in an antilateral relationship as the sensing unit according to the present invention. The signal from the sensing coil produced a signal to noise ratio of about 5 for the smallest hole on the side of the disk opposite of the magnet.

A table saw was fitted with a metal disc (without teeth). Flaws were simulated with drilled holes and/or slots in the metal disc. The metal disc rotated at about 3780 rpm resulting in a linear speed at 4.5 inch from center of about 8,900 feet per minute. Application of the magnetic field slowed the disc speed.

As the metal disc was rotated, the sensing unit was moved radially from the center of the rotating disc to the perimeter of the rotating disc. Accordingly, each flaw passed the sensing unit a plurality of times each time generating a signal. The plurality of signals for each flaw were used to quantify the area and/or volume of the flaw.

Inclusions were simulated with holes drilled in the disc of 0.020 inch diameter and depths from 25% to 100% (through) of the thickness of the disc.

EXAMPLE 2

Figure 6:
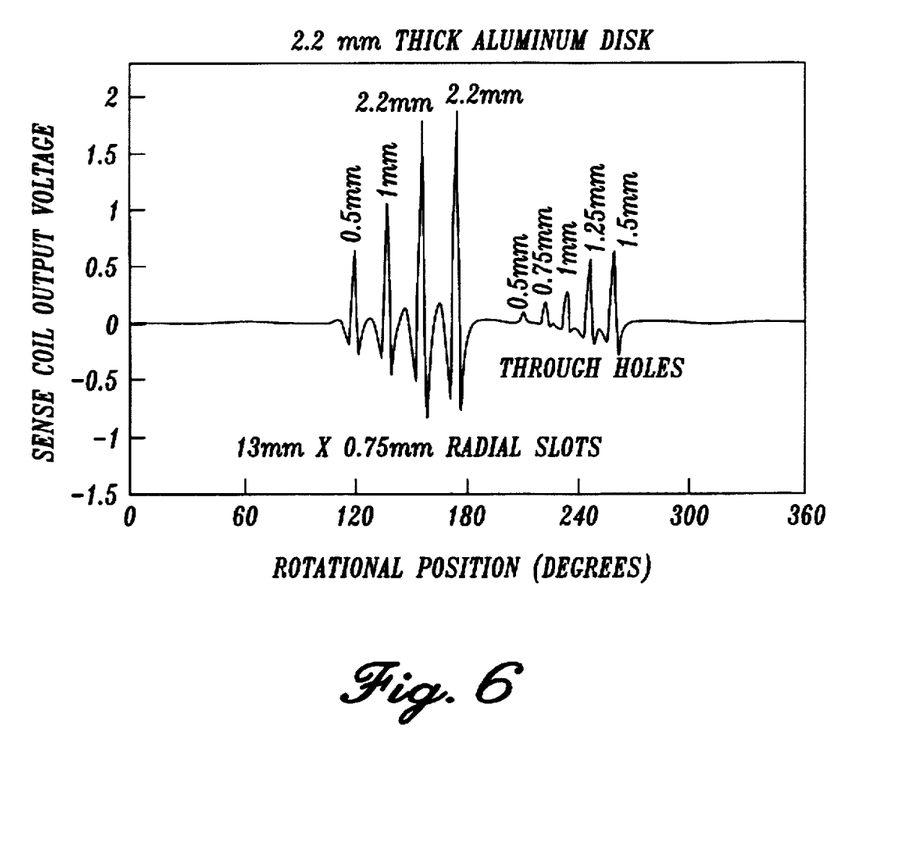
FIG. 6 is a graph of sensing coil voltage for radial slot and circular hole simulated inclusions.

Experimental apparatus as described in Example 1 was used for further testing with a 2.2 mm thick aluminum disc in accordance with the present invention. Through holes of diameters of 0.5 mm, 0.75 mm, 1 mm, 1.25 mm, and 1.5 mm were drilled to simulate inclusions. Also radial slots of 13 mm length by 0.75 mm width having depths of 0.5 mm, 1 mm, 2 mm, and 2.2 mm (through) were used. Sensing coil voltage for these inclusions are shown in FIG. 6.

EXAMPLE 3

Apparatus as described in Example 1 was further used with a steel disk prepared with simulated flaws as listed in Table E3.

TABLE E3

| | Simulated Flaw Characterization | | |
|---|---|---|---|
| Flaw | Through Hole Diameter (mm) | 0.5 mm Hole Percent Through | 0.5 mm Wide Notch Depth (mm) |
| 1 | 1.5 | | |
| 2 | 1.25 | | |
| 3 | 1.0 | | |

TABLE E3-continued

| | Simulated Flaw Characterization | | |
|---|---|---|---|
| Flaw | Through Hole Diameter (mm) | 0.5 mm Hole Percent Through | 0.5 mm Wide Notch Depth (mm) |
| 4 | 0.75 | | |
| 5 | 0.5 | | |
| 6 | | 50 (unilateral) | |
| 7 | | 25 (unilateral) | |
| 8 | | 50 (antilateral) | |
| 9 | | 25 (antilateral) | |
| 10 | | | 0.25 |
| 11 | 0.5 | | |

Figure 7A:
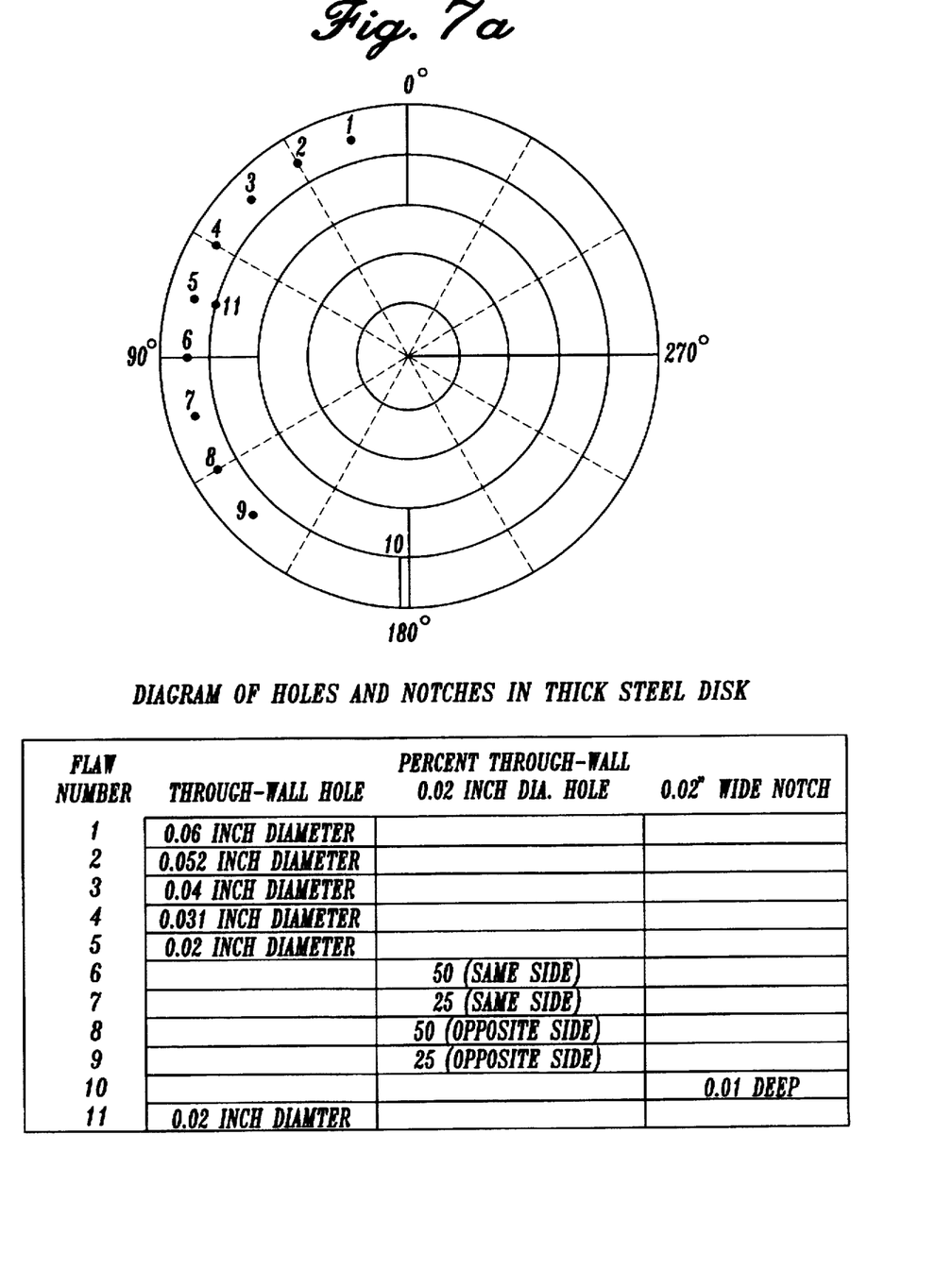
FIG. 7a is a flaw map for a steel disc.
Figure 7B:
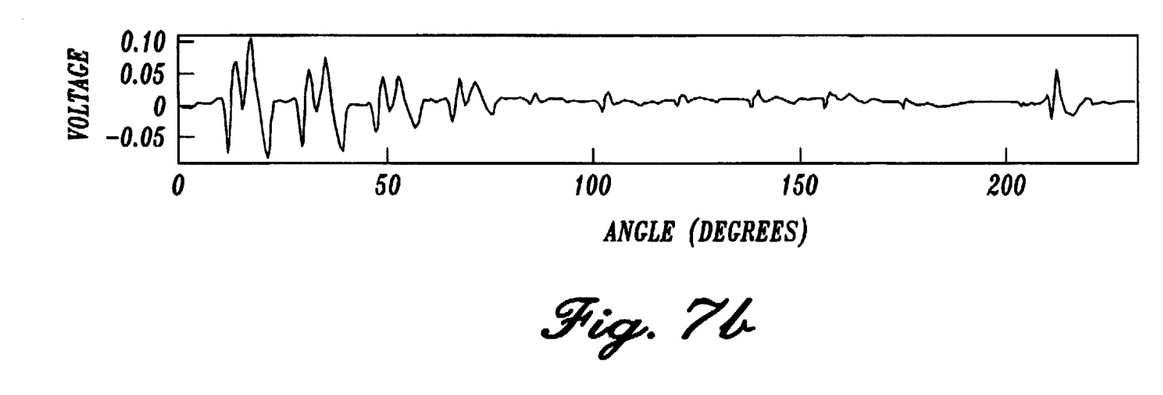
FIG. 7b is a sensing coil output for the flaws on the steel disc.
Figure 7C:
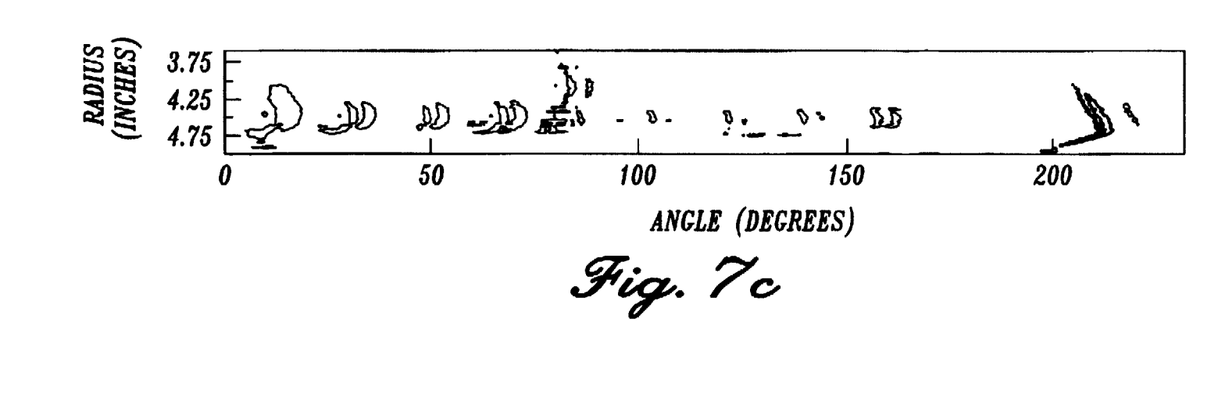
FIG. 7c is a contour plot of the flaws on the steel disc.

A flaw map is shown in FIG. 7a. Sensing coil voltages are shown in FIG. 7b with flaw cross section contours shown in FIG. 7c.

EXAMPLE 4

A further test was done with the apparatus as described in Example 1 with an aluminum disc 32 mm thick and 254 mm in diameter. Flaw characterization is given in TABLE E4. Slots are 0.8 mm long by 1.25 mm wide.

TABLE E4

| | | Flaw Characterization | |
|---|---|---|---|
| Flaw | Position | Hole Diameter (mm) | Slot Depth (mm) |
| 1 | 123° | | 0.5 |
| 2 | 142° | | 1.0 |
| 3 | 161° | | 2.0 |
| 4 | 180° | | Through |
| 5 | 218° | 0.5 (through) | |
| 6 | 231° | 0.75 (through) | |
| 7 | 244° | 1.0 (through) | |
| 8 | 257° | 1.25 (through) | |
| 9 | 270° | 1.5 (through) | |

Figure 8A:
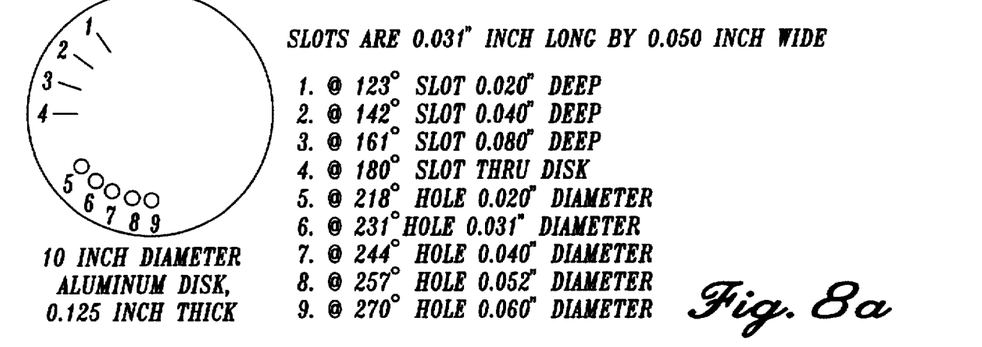
FIG. 8a is a flaw map for an aluminum disc.
Figure 8B:
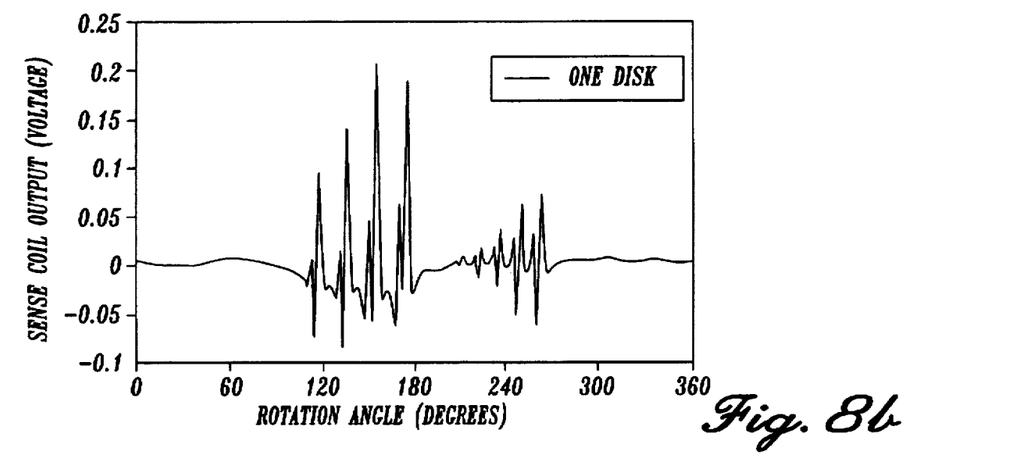
FIG. 8b is a sensing coil output for the flaws on the aluminum disc.
Figure 8C:
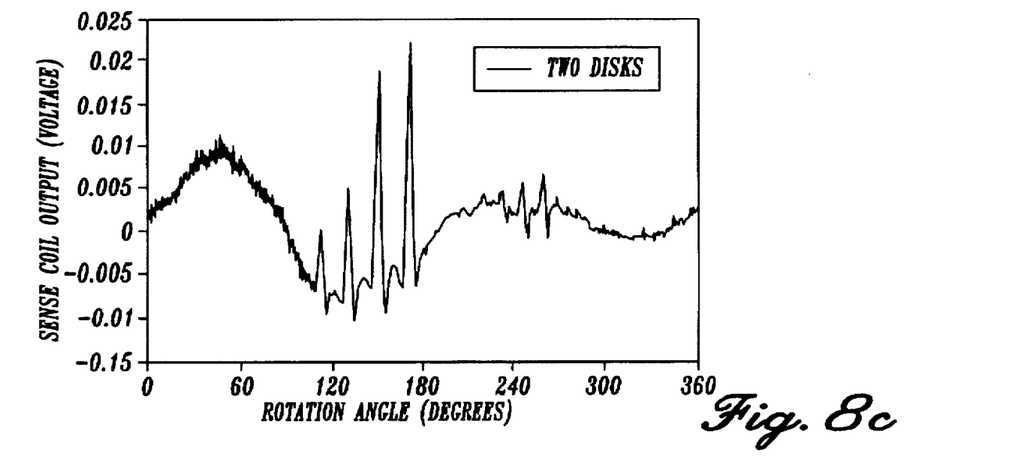
FIG. 8c. is a sensing coil output for the flaws on the aluminum disc covered by a second unflawed disc, simulating a laminate.

A flaw map is shown in FIG. 8a. Sensing coil output voltages are shown in FIG. 8b. A second non-flawed disk was placed over the flawed disc to simulate a laminate having subsurface flaws. The sensing coil output voltages of the laminate are shown in FIG. 8c.

For testing the present invention and for inspection of discs, tubes or other rotating piece, a single sensing unit experiencing a plurality of passes of each flaw is sufficient to determine flaw area and/or volume. However, for inspection of sheets or non-rotating pieces, a plurality of sensing units may be used to obtain a plurality of signals from a single flaw.

PORTABLE EMBODIMENT

Figure 9:
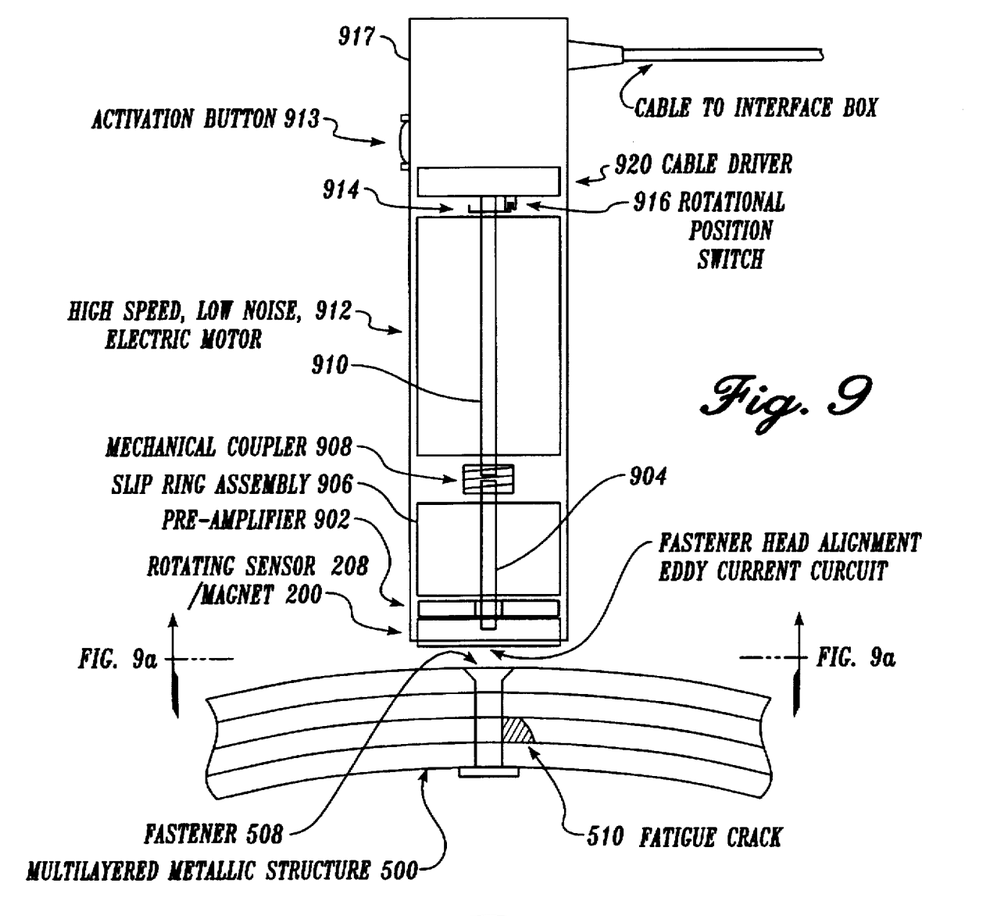
FIG. 9 is a cross section of a portable embodiment of the present invention.
Figure 9A:
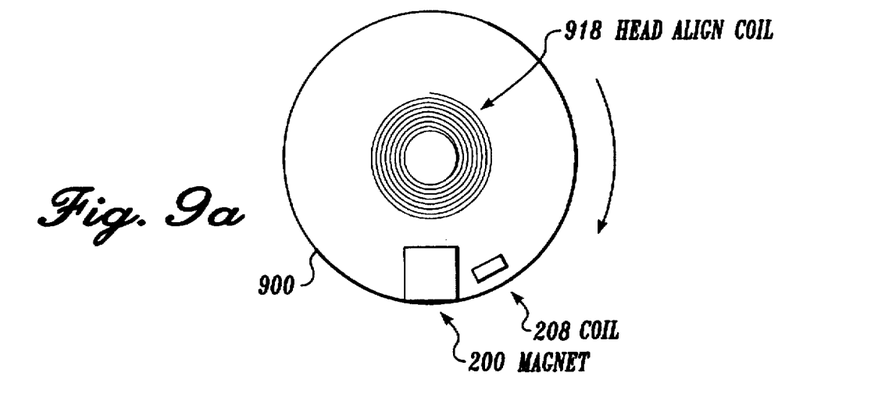

A portable embodiment of the present invention is shown in FIG. 9. The magnet 200 and sensing coil 208 are mounted eccentrically on a disk 900 in unilateral relationship. A pre-amplifier 902 is preferably mounted on the disk 900 to amplify signals from the sensing coil 208. The disk 900 is connected to a shaft 904 though a slip ring 906 into a mechanical coupler 908. The slip ring 906 permits transferring signals from the rotating sensing coil 208 to a stationary data collection device (not shown). A second shaft 910 is connected to the mechanical coupler 908 into a motor 912, preferably a high speed (up to about 500 rps), low noise electric motor. An activation button 913 is provided to operate the motor 912. The mechanical coupler 908 may be any coupler, but is preferably a flexible coupler. A second end 914 of second shaft 910 may be connected to a rotational position switch 916 used to correlate the sensing coil 208 signal with angular position. These components are preferably mounted in a housing 917.

In a preferred embodiment, an eddy current coil 918 is centrally mounted on the disk 900, specifically on the same side of the disk 900 as the magnet 200 and sensing coil 208 facing the multilayered metallic structure 500. The eddy current coil is used to sense a rivet or fastener 508 so that an operator knows when the portable embodiment is positioned over the fastener 508. The eddy current coil 918 may be attached to a light (not shown).

Further in a preferred embodiment, a cable driver 920 is used for impedance matching and signal noise reduction. A cable 922 provides power to the motor 912 and data signals to the data collection device.

CLOSURE

The data acquisition system may be used to make raster images of the conductive material showing location and severity of inclusions.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for detecting flaws in conductive material having a material surface, the apparatus having a sensing unit having a magnet having a substantially constant magnetic field, the magnet placed adjacent to one side of the conductive material, the magnet having a datum point that is a point located on a line through a center of the magnet and perpendicular to said material surface and on a plane defined by a magnet surface(s) facing the material surface, a sensing coil that is stationary with respect to the magnet wherein the magnet and sensing coil are in relative motion with respect to the conductive material, said sensing coil having a datum orientation with a longitudinal axis of the sensing coil perpendicular to the material surface, wherein the improvement comprises:

the sensing coil spaced apart from the magnet at a spacing that is less than one magnet dimension, the sensing coil further positioned away from a datum, the position selected from the group consisting of an antidatum position, an antidatum orientation and a combination thereof.

2. The apparatus as recited in claim 1, wherein said magnet is a flat magnet.

3. The apparatus as recited in claim 1, wherein said sensing coil is in an antilateral relationship with respect to the magnet and the conductive material.

4. The apparatus as recited in claim 1, wherein said sensing coil is in unilateral antidatum relationship with respect to the magnet and the conductive material.

5. The apparatus as recited in claim 1, wherein said sensing coil is tilted.

6. The apparatus as recited in claim 1, wherein said flaw passes said sensing unit a plurality of times.

7. The apparatus as recited in claim 1, wherein said flaw passes a plurality of sensing units.

8. A method for detecting flaws in conductive material having a material surface, the method having the steps of providing a sensing unit having a magnet having a substantially constant magnetic field, placing the magnet adjacent to one side of the conductive material, the magnet having a datum point that is a point located on a line through a center of the magnet and perpendicular to said material surface and on a plane defined by a magnet surface(s) facing the material surface, providing a sensing coil that is stationary with respect to the magnet wherein the magnet and sensing coil are in relative motion with respect to the conductive material, said sensing coil having a datum orientation with a longitudinal axis of the sensing coil perpendicular to the material surface, wherein the improvement comprises:

positioning the sensing coil apart from the magnet at a distance that is less than one magnet dimension, further positioning the sensing coil away from a datum, the position selected from the group consisting of an antidatum position, an antidatum orientation and a combination thereof.

9. The method as recited in claim 8, wherein said magnet is a flat magnet.

10. The method as recited in claim 8, wherein said antidatum position of the sensing coil is an antilateral relationship with respect to the magnet and the conductive material.

11. The method as recited in claim 8, wherein said antidatum position of the sensing coil is unilateral antidatum relationship with respect to the magnet and the conductive material.

12. The method as recited in claim 8, wherein said sensing coil is tilted.

13. The method as recited in claim 8, further comprising the step of passing said flaw passes past said sensing unit a plurality of times.

14. The method as recited in claim 8, wherein further comprising the step of passing said flaw past a plurality of sensing units.

15. The method as recited in claim 13, further comprising the step of making a contour plot of said flaw.

16. The method as recited in claim 14, further comprising the step of making a contour plot of said flaw.

* * * * *